United States Patent [19]

Grützke et al.

[11] Patent Number: 5,668,275
[45] Date of Patent: Sep. 16, 1997

[54] PROCESS FOR BLEACHING ALKYL POLYGLYCOSIDES

[75] Inventors: Jürgen Grützke, Bochum; Stefan Schmidt, Haltern, both of Germany

[73] Assignee: Huels Aktiengesellschaft, Marl, Germany

[21] Appl. No.: 525,345

[22] Filed: Sep. 7, 1995

[30] Foreign Application Priority Data

Sep. 7, 1994 [DE] Germany .................. 44 31 852.9

[51] Int. Cl.⁶ .................. C07H 1/06; C07H 15/04
[52] U.S. Cl. .................. 536/127; 536/18.5; 536/120; 536/123.1; 536/124
[58] Field of Search .................. 127/34; 536/18.5, 536/18.6, 123.1, 120, 124, 127

[56] References Cited

U.S. PATENT DOCUMENTS

| | | | |
|---|---|---|---|
| 4,223,129 | 9/1980 | Roth et al. | 536/4.1 |
| 5,206,357 | 4/1993 | Schmidt | 536/18.6 |
| 5,227,480 | 7/1993 | Oberholz et al. | 536/18.5 |
| 5,420,262 | 5/1995 | Schmidt | 536/18.6 |
| 5,432,275 | 7/1995 | McCurry et al. | 536/124 |
| 5,461,144 | 10/1995 | Kahsnitz et al. | 536/18.5 |
| 5,527,892 | 6/1996 | Borsotti et al. | 536/18.6 |
| 5,554,740 | 9/1996 | McCurry et al. | 536/4.1 |

FOREIGN PATENT DOCUMENTS

| | | |
|---|---|---|
| 0035589 | 9/1981 | European Pat. Off. . |
| 0 165 721 | 12/1985 | European Pat. Off. . |
| 0 306 652 | 3/1989 | European Pat. Off. . |
| 389753 | 10/1990 | European Pat. Off. . |
| 3940827 | 6/1991 | Germany . |
| 41 01 252 | 7/1992 | Germany . |
| 4234241 | 4/1994 | Germany . |
| WO91/09043 | 6/1991 | WIPO . |

*Primary Examiner*—John Kight
*Assistant Examiner*—Howard C. Lee
*Attorney, Agent, or Firm*—Oblon, Spivak, McClelland, Maier & Neustadt, P.C.

[57] ABSTRACT

The application relates to a novel process for bleaching alkyl polyglycosides having $C_8$- to $C_{20}$-alkyl groups in aqueous solution using peroxy compounds. The bleaching is carried out in a tubular reactor.

8 Claims, No Drawings

PROCESS FOR BLEACHING ALKYL POLYGLYCOSIDES

BACKGROUND OF THE INVENTION

1. Field of the Invention

The invention relates to a process for bleaching alkyl polyglycosides, in which the alkyl groups have 8 to 24 C atoms, are bleached in aqueous solution by peroxy compounds in a tubular reactor.

2. Discussion of the Background

Alkyl polyglycosides are non-toxic and readily degradable surfactants. They are therefore used as washing and cleaning agents and as emulsifiers and dispersants. However, they only have the desired surfactant properties when the alkyl groups have at least 8 C atoms.

Alkyl polyglycosides having long-chain alkyl groups are generally prepared by single-stage or multistage syntheses.

A single-stage preparation process is described inter alia in DE-A-41 01 252.

A two-stage process is specified for example in EP-A-0 306 652, according to which an n-butyl glycoside is first prepared by glycosidation with n-butanol and the desired long-chain alkyl polyglycoside is thereupon prepared by transglycosidation with a long-chain alcohol.

During the preparation of the alkyl polyglycosides, product discolorations occur due to undesired oxidation and condensation processes. The technological properties are not affected by this. However, the disadvantageous visual impression makes it more difficult to market the products. In order to improve the color quality, alkyl polyglycosides are therefore generally subjected to a bleaching process after their preparation. For this purpose they are first neutralized and excess fatty alcohol is distilled off, whereupon the bleaching is then performed in aqueous solution.

According to EP-A-0 165 721, the color of alkyl polyglycoside solutions can be improved by multistage bleaching using hydrogen peroxide and stabilized by addition of compounds releasing sulphur dioxide. Because of the high volatility of hydrogen peroxide, this bleaching is carried out in a closed vessel at 1 to 20 bar.

Bleaching is normally performed in stirred tanks. However, these reactors have an unfavorable broad residence time spectrum for a continuous mode of operation and lead to a broad spectrum of reaction products. As a result, a high additional expenditure in terms of apparatus is required to avoid the disadvantages.

The object of the present invention was to provide an improved process for bleaching. In particular, the aim was to avoid the disadvantages of bleaching in the conventional equipment of the prior art.

SUMMARY OF THE INVENTION

According to the invention, the object is achieved by carrying out the bleaching in a tubular reactor.

DETAILED DESCRIPTION OF THE PREFERRED EMBODIMENTS

Suitable tubular reactors generally have a diameter of 0.5 to 50 cm and a length of 0.5 to 50 m, where the length is to be at least 4 times the diameter. In the simplest case this is a heatable tube. However, the tubular reactor preferably also has a plurality, usually 1 to 20, of inlet points. Bleaching agent and aqueous alkaline solution for pH adjustment can then be metered in subsequently via these inlet points.

The tubular reactor can also contain chicanes and vortex-inducing internals, for example inline mixers. The tube can be arranged horizontally, at an incline or vertically. Thus substrate and bleaching agent, despite co-current flow conditions, are mixed together very well. Stirred tanks can also be connected upstream and downstream of the tubular reactor.

Suitable bleaching agents are, for example, hydrogen peroxide, ozone, perborate, sodium hypochlorite, percarbonate, peracetate or peroxodisulphate. Hydrogen peroxide is preferred.

The aqueous alkyl polyglycoside solutions are preferably 30 to 90% strength, and are prepared by conventional means known to those of ordinary skill in the art. 40 to 70% strength solutions are particularly preferred for the bleaching.

In the preparation of the alkyl polyglycosides, the saccharides used can be glucose, mannose, galactose, talose or fructose. The preferred saccharide is glucose.

The alkyl chains are derived from alcohols such as octanol, decanol, lauryl alcohol, myristyl, palmityl and stearyl alcohol.

The alkyl polyglycosides generally have a mean degree of glycosidation of 1 to 5, products having mean degrees of glycosidation of 1.1 to 2 being preferably and mean degrees of glycosidation of 1.1 to 1.4 being very particularly preferably used.

The bleaching is usually performed at 50° to 120° C. and a pressure of 1 to 10 bar.

Alkyl polyglycosides can be uniformly bleached by the present process with a narrow residence time distribution. Bleaching agents and other auxiliaries can be metered exactly in this case into simple equipment. The bleaching process can be carried out discontinuously and also continuously without problem. Light-colored products having iodine color values below 20 are obtained in this case (with 50% strength solutions).

Other features of the invention will become apparent in the course of the following descriptions of exemplary embodiments which are given for illustration of the invention and are not intended to be limiting thereof.

EXAMPLE 1

20 kg per hour of an aqueous alkyl polyglycoside solution (water content: 43%, iodine color value: 60, pH: 8) and 0.6 kg of a 35% strength $H_2O_2$ solution are fed to a heatable tube (diameter: 50 mm, length: 1.5 m). A static mixer is connected upstream of the tubular reactor, in which the two solutions are homogeneously mixed in the static mixer. The mean reactor interior temperature is set by a tube heater to 75° C. The pH is kept approximately constant by addition of sodium hydroxide solution through 2 nozzles after one third and after two thirds of the reactor length. 2 inline mixers ensure satisfactory homogenization in the reactor.

At the exit of the tubular reactor the aqueous alkyl polyglycoside solution has an iodine color value of 5.

Obviously, numerous modifications and variations of the present invention are possible in light of the above teachings. It is therefore to be understood that within the scope of the appended claims, the invention may be practice otherwise than as specifically describe therein.

This application is based on German Patent Application P 44 31 852.9, filed in the German Patent Office on Sep. 7, 1994, the entire contents of which are hereby incorporated by reference.

What is claimed as new and desired to be secured by Letters Patent of the United States is:

1. A process for bleaching alkyl polyglycosides having $C_8$- to $C_{20}$-alkyl groups in aqueous solution using a bleaching agent comprising bleaching in a tubular reactor, an alkyl polyglylcoside having $C_{8-20}$ alkyl groups in an aqueous solution with a bleaching agent.

2. The process of claim 1, wherein said bleaching is performed in a tubular reactor having 1 to 20 inlet points, and bleaching agent and aqueous alkaline solution are metered in subsequently via these inlet points.

3. The process of claim 1, wherein said bleaching is performed in a tubular reactor having inline mixers.

4. The process of claim 1, wherein said bleaching agent is hydrogen peroxide.

5. The process of claim 1, wherein a 30 to 90% strength aqueous alkyl polyglycoside solution is bleached.

6. The process of claim 1, wherein a 40 to 70% strength aqueous alkyl polyglycoside solution is bleached.

7. A process for bleaching alkyl polyglycosides, comprising the step of bleaching an aqueous solution of an alkyl polyglycoside having $C_{8-20}$ alkyl groups with a bleaching reagent in a tubular reactor, wherein said tubular reactor has a diameter of 0.5 to 50 cm, a length of 0.5 to 50 m and where the length is at least four times the diameter.

8. The process of claim 7, wherein said tubular reactor contains inline mixers.

* * * * *